(12) United States Patent
Klinger

(10) Patent No.: US 6,569,808 B2
(45) Date of Patent: May 27, 2003

(54) METHODS AND COMPOSITIONS USEFUL FOR BRYOPHYTE REMEDIATION TO IMPROVE FOREST HEALTH AND GROWTH

(76) Inventor: Lee F. Klinger, 2125 Mariposa Ave., Boulder, CO (US) 80302

( * ) Notice: Subject to any disclaimer, the term of this patent is extended or adjusted under 35 U.S.C. 154(b) by 0 days.

(21) Appl. No.: 09/918,315

(22) Filed: Jul. 30, 2001

(65) Prior Publication Data

US 2003/0027721 A1 Feb. 6, 2003

(51) Int. Cl.$^7$ .......................... A01N 25/24; A01N 59/06
(52) U.S. Cl. ...................... 504/119; 504/120; 504/121; 504/123; 504/187; 47/DIG. 10
(58) Field of Search ................................ 504/119, 120, 504/121, 123, 187, 116.1; 47/DIG. 10

(56) References Cited

U.S. PATENT DOCUMENTS

| | | | | |
|---|---|---|---|---|
| 6,287,356 B1 | * | 9/2001 | Wommack et al. | 71/28 |
| 2001/0018047 A1 | * | 8/2001 | Rose et al. | 424/78.31 |

OTHER PUBLICATIONS

Whitcher, Steve. "Moss Control in Lawns". http://gardening.wsu.edu/library/lawnOO3/lawnOO3. 1996.*
Cook, T. W., et al. "Controlling Moss in Lawns", Oregon State U. Extension Service. FS 55. May 1998.*
Peak Materials Azomite, Inc., "What is Azomite?," 2000.
Lee F. Klinger; "Coupling of Soils and Vegetation in Peatland Succession," Arctic and Alpine Research, vol. 28, No. 3, 1996, pp. 380–387.
Monique Cornish, "Forest Decline as a Successional Process: The Role of Bryophytes in a Montane Ecosystem in the Colorado Rocky Mountains," Sep. 1999.
Olle Zackrisson, Gisela Norberg, Ann Dolling, Marie–Charlote Nilsson, and Anders Jaderlund, "Site preparation by steam treatment: effects on forest vegetation control and establishment, nutrition, and growth of seeded Scots pine," Swedish University of Agricultural Sciences, Faculty of Forestry, Department of Forest Vegetation Ecology, S–901 83 Umea, Sweden. Can. J. For. Res. 27:315–322 (1997).
G. Norberg, A. Jaderlund, O. Zackrisson, T. Nordfjell, D.A. Wardle, M.–C. Nilsson, A. Dolling, "Vegetation control by steam treatment in boreal forests: a comparison with burning and soil scarification," Can. J. For. Res. 27:2026–2033 (1997).

Lee F. Klinger, "Memoirs of the Torrey Botanical Club," vol. 24, No. 1; Jun. 1990.

* cited by examiner

*Primary Examiner*—S. Mark Clardy
(74) *Attorney, Agent, or Firm*—Steven C. Petersen; Hogan & Hartson, LLP

(57) ABSTRACT

The present invention provides a novel composition and method for controlling, killing or inhibiting the growth of bryophytes (e.g. mosses and liverworts). It is applicable to the remediation of these organisms in, gardens, orchards or agricultural land, or forests and upon higher plants without substantial detriment to grasses, trees or most broad leaf plants. The novel composition is a combination of an effective amount of finely ground calcium-rich compound suspended in a horticulturally or agriculturally acceptable diluent, and/or binder/carrier. In addition to being a carrier for the calcium-rich compound the binder also acts to bind fine soil particles, helping to conserve irrigation water and to reduce soil erosion. The binder can further incorporate further components such as wetting agents and penetration agents (both of which are broadly referred to as surfactants), and translocation agents, adhesives, emulsifiers, suspending agents, thickeners, synergists other moss killers or biocides, such as herbicides, fungicides, bactericides, insecticides and weed killers, hormones, plant growth regulators or plant nutrients.

18 Claims, 1 Drawing Sheet

(1 of 1 Drawing Sheet(s) Filed in Color)

METHODS AND COMPOSITIONS USEFUL FOR BRYOPHYTE REMEDIATION TO IMPROVE FOREST HEALTH AND GROWTH

BACKGROUND OF THE INVENTION

1. Field of the Invention

The present invention relates to a bryocidal formulation and methods of use that are useful in the management and control of bryophytes. More specifically, the bryocidal formulation and methods of use thereof are useful in slowing and/or reversing the decline in the quality and health of mature trees.

2. Description of the State of Art

Scientists worldwide have been puzzled by a seemingly rapid decline in the quality and health of many mature and old-growth forests. Interestingly, forests most protected from the impact of natural and human disturbances often seem to be suffering the worst. Because so many causes have been postulated for forest decline, ranging from acid rain and global warning to pathogenic fungi and viruses, most scientists now accept a "multiple factor" explanation for tree dieback. Indeed, it is common for forests in decline to be simultaneously affected by both environmental stresses (e.g., drought, acid rain, and soil acidification) and biological stresses (e.g., root rot, bark beetles, and budworms). However, since the list of possible causes varies from species-to-species and place-to-place, the utility of such characterizations becomes problematic. Conventional approaches have yet to yield any unified set of mechanisms, which can account for forest decline globally.

Accordingly, solutions to remediate the problem of forest decline have focused on treating the various causal factors where they occur. Treatments include fumigating for insects and soil pathogens, applying lime, calcium-rich fertilizers, or leaf mulch to reduce soil acidity, and reducing levels of acid rain by controlling pollution. Of these treatments, liming has been shown to be the most effective, though it has not always resulted in improved forest health. None of these methods have proven to be a general solution to widespread forest decline.

Besides the problem of decline in mature and old-growth forests, there has also been found to be a problem in seedling regeneration following logging of these forests. Various site preparation techniques have been found to promote the establishment of seedlings that naturally regenerate or are subsequently planted. The techniques include prescribed burning, herbicides, scarification (scraping of surface soils), raking, and applying steam. These treatments are intended to remove or kill the remaining ground vegetation after logging, thus allowing for greater survival and growth of tree seedlings. All of these techniques have been shown to be effective, in varying degrees, in promoting seedling regeneration, however these techniques are used only for site preparation and not in the maintenance of older trees or forests.

In addition to natural forests, the agriforest and timber industries of the world are profoundly impacted by forest decline and the economical and social benefits that would be achieved through the slowing and/or reversal of forest decline would be enormous. For instance, in the state of Florida citrus trees produce over $1 billion gross revenues annually. Effective treatments for controlling citrus decline could add on the order of $10 to $100 million in revenues annually to the Florida citrus industry alone. Considering the extent of citrus plantations and other forests managed for agricultural and timber production that are affected by forest decline, the financial benefit of an effective treatment method on these industries is likely in the billions of dollars.

A major breakthrough in forest decline research, achieved by applying complex system theory to the problem, has revealed the critical role that forest floor mosses play in weakening and killing trees, see FIG. 1. Moss effects are primarily via the chemical modification of water that passes though their tissues and then into the underlying root zone. Fine roots are killed by the heavy metal compounds which are contained in this highly acidic leachate. Affected trees have difficulty obtaining water from the soils and become water stressed, which manifests itself initially through the decline and death of the uppermost leaves and branches. Virtually all symptoms typical of forest decline are consistent with an overall loss of fine roots.

As discussed above, foresters have used steam while preparing the ground for reseeding with coniferous seedlings after logging. Steaming as ground preparation is part of a general strategy to release nutrients from the soil and to remove vegetation. Additionally, although previously foresters have treated forests with lime, calcium-rich fertilizers, or leaf mulch to rejuvenate forests, such treatments were aimed at reducing soil acidity. Consequently, such fertilizers were formulated and such treatments were performed in a manner whereby the fertilizers would penetrate the soil surface and not be retained thereon. Consequently, these techniques had little to no impact on forest floor moss.

Bryophyte remediation (or "bryo-remediation") refers to a suite of practices, which are specifically focused on reducing the growth and cover of bryophytes (e.g., mosses and liverworts), to the benefit of the surrounding trees. Certain "traditional" forestry practices, as discussed above, such as prescribed fires, applying lime, and raking, all of which tend to lessen the acidity of forest soils, also act, more or less, as moss reduction techniques. However, no specific formulation has been developed to directly suppress moss growth. Although scientists have recognized the deleterious effects of mosses on mature trees and forests, there is further a need for a satisfactory means by which to reduce moss beneath mature trees thus benefiting the overall health of trees and forests.

SUMMARY OF THE INVENTION

The present invention provides novel compositions and methods for controlling, killing or inhibiting the growth of bryophytes (e.g. mosses and liverworts). It is applicable to the killing of these organisms in, gardens, orchards or agricultural land, forests and upon higher plants without substantial detriment to grass, trees or most broad leaf plants. The novel composition is a combination of an effective amount of a finely ground calcium-rich compound suspended in a horticulturally or agriculturally acceptable diluent, and/or binder/carrier. In addition to being a carrier for the calcium-rich compound the carrier also acts to bind fine soil particles, helping to conserve irrigation water and to reduce soil erosion. The bryocidal formulation may be applied directly to untreated soils or alternatively the soil may be pretreated by the use of steam.

Additional advantages, and novel features of this invention shall be set forth in part in the description and examples that follow, and in part will become apparent to those skilled in the art upon examination of the following or may be learned by the practice of the invention. The advantages of the invention may be realized and attained by means of the instrumentalities and in combinations particularly pointed out in the appended claims.

BRIEF DESCRIPTION OF THE DRAWINGS

The file of this patent contains at least one drawing executed in color. Copies of this patent with color drawings will be provided by the Patent and Trademark Office upon request and payment of the necessary fee. The accompanying drawings, which are incorporated in and form a part of the specification, illustrate the preferred embodiments of the present invention, and together with the description serve to explain the principles of the invention.

In the Drawings

DETAILED DESCRIPTION OF THE PREFERRED EMBODIMENT

Figure 1:
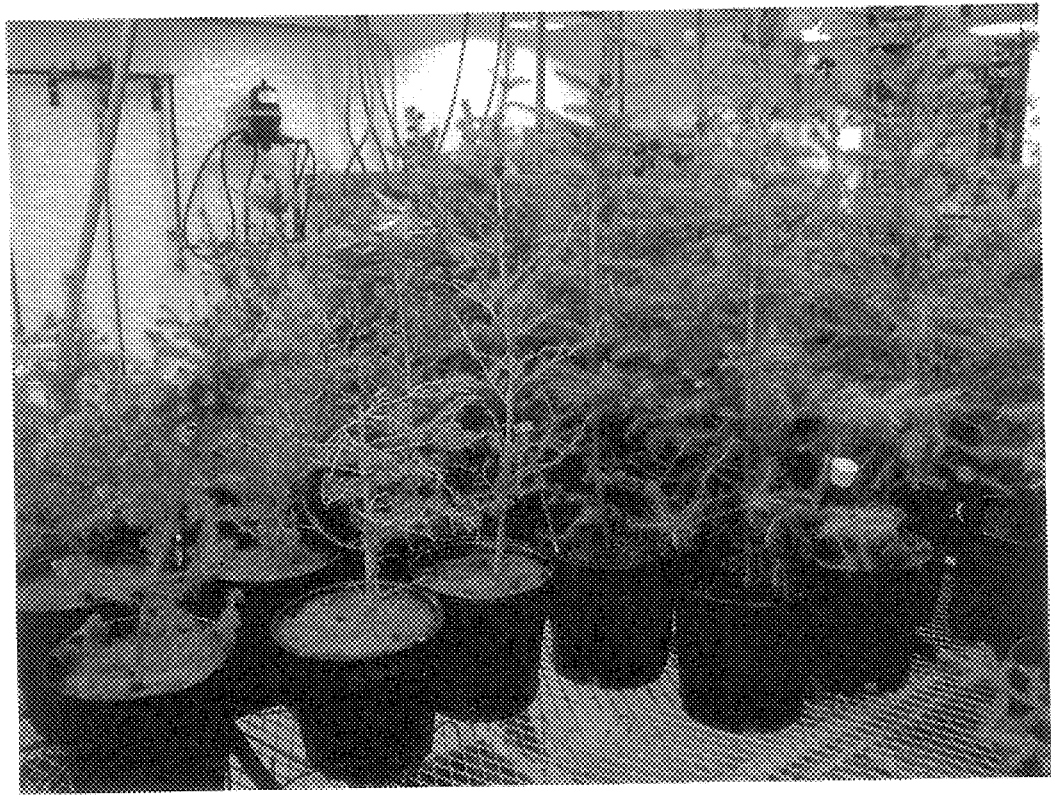
FIG. 1 is a photograph depicting the effects of bryophytes on trees.

The present invention relates to a bryocidal composition or formulation which incorporates a calcium-rich compound, such as a naturally mined rock (AZOMITE™, also referred to herein as azomite) which chemically is a hydrated sodium calcium aluminosilicate. This bryocidal composition acts primarily upon bryophytes (i.e., mosses and liverworts.) The bryocidal formulation is a combination of an effective amount of finely ground AZOMITE™ or a similar calcium-rich compound suspended in a horticulturally or agriculturally acceptable diluent, and/or carrier/binding agent. In addition to being a carrier for the AZOMITE™ the carrier also acts to bind fine soil particles, helping to conserve irrigation water and to reduce soil erosion. The carrier can further incorporate further components such as wetting agents and penetration agents (both of which are broadly referred to as surfactants), and translocation agents. It is totally unexpected that the formulation of the present invention would have bryophyte-controlling activity since the active agent, AZOMITE™, is currently approved for organic farming in many western states for use as a fertilizer.

Informed by the new breakthroughs in understanding moss-soil-root dynamics and their relation to canopy dynamics, the present invention focuses on improved, and targeted, bryo-remediation techniques that can stop forest decline and promote the healthy rejuvenation of affected trees. In light of the surprising discovery that the bryocidal composition of the invention directly controls bryophytes when formulated to remain on the soil surface the present invention is further directed towards methods of applying the bryocidal compositions to control bryophyte growth and formation under trees, plantations and in forests. One of the bryocidal compositions of the present invention, referred to herein as SILVICURE™, aggressively controls the deleterious growth and spread of bryophytes with little or no impact on other parts of the ecosystem. This composition of the present invention and methods of use thereof can be used as a tool for significantly improving tree health and productivity.

The present invention relates to compositions and methods to improve health of forests and mature trees. Improving health of trees can include, but is not limited to, preventing tree dieback, and increasing the productivity of the tree whether by way of fruit production, wood production, pulp production, sap production (i.e., in the form of syrup), and/or flower production. Other benefits achieved by improving health of trees can include, but are not limited to, stabilizing soils, sheltering and/or providing habitat for other plants and/or animals, reducing susceptibility to fire, greater safety by decreasing tree fall, increasing carbon uptake from the atmosphere, and increasing the aesthetic value of forests.

Tree dieback refers to tree decline that begins with death of the top branches or the ends of outer branches, and then progresses downward or inward along the outer branches to the trunk. Improving health of trees also refers to preventing and reducing the death of the feeder roots of trees. Improving health of trees also can include improving the growth of trees. Such improvement in growth can take the form of preventing a decrease in trunk diameter rate of growth.

Compositions and methods of the current invention are particularly useful for problems related to acid rain. Acid rain stimulates bryophyte growth, leading to accelerated forest decline. Controlling bryophyte growth with these compositions and methods can thus prevent or mitigate the effects of acid rain.

The term, bryophyte remediation, or control of bryophytes, includes, but is not limited to, reducing the growth of bryophytes, reducing the area covered by bryophytes, and/or killing bryophytes directly. The bryocidal formulation of the present invention can refer to compounds and/or formulations that remediate bryophytes, without substantial detriment to grasses, trees, or other plants.

The term "trees" refers to all woody angiosperms and gymnosperms in both a natural and commercial setting, and refers both to saplings (i.e. immature trees) and mature trees. The invention contemplates use on any tree species that may be benefited by the treatments of the invention. In a preferred embodiment, trees to be treated include all trees used for timber, bananas, coconut palm, olives, ground nuts, oil palm, roses, lucerne, sugar maples, tea and fruit, including citrus fruit, apples, plums, peaches, oranges, nectarines, mangoes, pears, cherries, grapes, berries, currants, dates, figs, avocados, almonds, and apricots.

Other crops and crop plants which are not be trees but are nonetheless of importance which may be protected according to the present invention include sugar cane, alfalfa, hemp, flax, peanuts, sorghum, alliums including onions, shallots, leeks, garlic, chives and spring onions, root vegetables including carrots, parsnips, turnips, beetroot, sugar beet, radishes, swedes and mangolds, brassicas including cabbages, broccoli, cauliflower and sprouts; grazing land pulses including peas, broad beans, French beans, runner beans, navy beans, kidney beans and lentils; curcubaceous plants including cucumbers, marrows, gourds and squashes, oilseed rape, timber, rubber, cotton, coffee, cocoa, jute, tomatoes, potatoes, yams, and/or tobacco.

Compositions of the present invention for bryophyte remediation include a soil treatment that includes a binding agent as well as a calcium-rich compound. Without being bound by theory, the inventor believes that calcium has a deleterious effect on bryophytes. Thus, any calcium-rich compound can be included in compositions of the present invention, and as such, a preferred calcium-rich compound includes, but is not limited to, hydrated sodium calcium aluminosilicate containing other minerals and trace elements which the National Research Council recognizes as being essential, herein referred to as AZOMITE™. AZOMITE™ is a registered trademark of Peak Minerals—AZOMITE, Inc., Branson, Mo. Other suitable calcium-rich compounds contemplated for use in this invention are crushed or micronized limestone, including rock dust, lime pulp, crushed or micronized seashells, crushed or micronized dolomite, and/or calcium ions in solution having a pH less than 7. The chemical composition of limestone is $CaCO_3$; of dolomite is $CaMg(CO_3)_2$. Lime pulp refers to the lime-rich byproduct of wood pulp production. Micronization refers to the process of finely grinding a mineral until particle sizes range from one micron in diameter to about 1 millimeter in diameter.

As way of illustration only, the bryocidal formulations discussed in detail below are prepared using AZOMITE.™ The bryocidal formulation is achieved by adding micronized (i.e., finely ground) AZOMITE™, in particle sizes ranging from about 30 microns in diameter to about 5 millimeters in diameter, to a suspension or solution of binder/carrier, such as a micronized biodegradeable copolymer, such as but not limited to, micronized polyacrylamide (PAM). Particle sizes of calcium-rich compounds can vary between about 30 microns in diameter and about 5 millimeters in diameter. More preferred are particle sizes that range from about 50 microns in diameter and about 200 microns in diameter. However, the larger particles in the millimeter size range may be effective for releasing calcium over prolonged periods of time, similar to a time release device.

Binders or carriers include, but are not limited to, any inert, nontoxic agent that will hold a calcium-rich compound on the soil surface for a length of time. One such class of carriers includes, but is not limited to, anionic polyacrylamides. A preferred carrier is micronized polyacrylamide (i.e., PAM). The micronized copolymers can have a particle size ranging from about 30 microns in diameter to about 700 microns in diameter, with most preferred sizes ranging between about 100 microns in diameter to about 300 microns in diameter.

Subsequently, if desired, other ingredients, such as surfactants, that is wetting agents or other binding agents, penetration agents, translocating agents, adhesives, emulsifiers, suspending agents, thickeners, synergists other moss killers or biocides, such as herbicides, fungicides, bactericides, insecticides and weed killers, hormones, plant growth regulators or plant nutrients may be added. The mixture is stirred until thoroughly mixed. An example of conditions that will result in thorough mixing includes, but is not limited to, stirring for 1 hour per 50 kilogram of mixture at a temperature between 20° C. and 30° C., with 25° C. being preferred. However, the skilled artisan will recognize that a wide variety of mixing conditions will result in a thoroughly mixed formulation of the invention. Since the solubility of AZOMITE™ is very low, the combination of micronizing it into fine particles, and then mixing it with a micronized biodegradeable copolymer, creates a resulting slurry that both benefits application effectiveness, and AZOMITE™ solubility and adsorption, while minimizing AZOMITE™ post-application leaching loss.

The preparations generally contain about 0.5% by weight and up to about 10% by weight of AZOMITE,™ with about 2% being preferred, and about 1% by weight and up to about 10% by weight of binder such as PAM, with about 3% being preferred. Percentages by weight of other calcium-rich compounds useful in the current invention will be similar to that of AZOMITE,™ and can be determined easily by the skilled artisan. Optimum concentrations of carrier can also be determined easily by the skilled artisan. It is contemplated that both the AZOMITE™ and the binder may be suspended in a surfactant that acts as the wetting agent. Surfactants that may be mixed with the azomite and the copolymer include nonionic surfactants such as tweens, carboxymethyl cellulose, glycols, akrylarylpolyoxyethylene ethers (X-77® a registered mark of Loveland Industries, Inc., Greeley, Colo.), alkyl polyoxyethylene ethers, polyethylene glycol p-isooctyl-phenyl ether (Triton X-100) aliphatic oxylated alcohols, ethoxylated soybean oils, hydrogenated castor oils, vegetable oils, methylated seed oils, pyrroles, N-alkylpyrrolidone ranging form $C_1$ to $C_{12}$ in alkyl length, and polyvinyl pyrrolidones. These surfactants may be used either alone or mixed.

Formulations
An example of a basic formulation:

| | Raw Materials | By Weight | Range |
|---|---|---|---|
| (1) | Calcium-rich compound | 2% | 0.5–10% |
| (2) | Binder | 3% | 1–10% |
| (3) | Solvent (Water) | 95% | 80–98.5% |

A second example of a formulation:

| | Raw Materials | By Weight | Range |
|---|---|---|---|
| (1) | Azomite ™ | 2% | 0.5–10% |
| (2) | Polyacrylamide | 3% | 1–10% |
| (3) | Water | 95% | 80–98.5% |

A third example of a formulation:

| | Raw Materials | By Weight | Range |
|---|---|---|---|
| (1) | Calcium-rich compound | 2% | 0.5–10% |
| (2) | Binder | 3% | 1–10% |
| (3) | Penetration agent | 1% | 0.1–10% |
| (4) | Water | 94% | 98.4–70% |

A fourth example of a formulation:

| | Raw Materials | By Weight | Range |
|---|---|---|---|
| (1) | Calcium-rich compound | 2% | 0.5–10% |
| (2) | Binder | 3% | 1–10% |
| (3) | Wetting agent | 1% | 0.1–10% |
| (4) | Water | 94% | 98.4–70% |

A fifth example of a formulation:

| | Raw Materials | By Weight | Range |
|---|---|---|---|
| (1) | Crushed lime, lime pulp, crushed shells, crushed dolomite | 2% | 0.5–10% |
| (2) | Binder | 3% | 1–10% |
| (3) | Water | 95% | 98.5–80% |

In one embodiment, the ground around trees and crop plants are treated with high pressure steam in conjunction with a bryocidal formulation disclosed above to control bryophytes and improve forest health. As discussed previously, foresters have used steam while preparing the ground for reseeding with coniferous seedlings after logging. Steaming as ground preparation is part of a general strategy to release nutrients from the soil and to remove vegetation. However, until the present invention, it has not been recognized that steam treatment applied to the ground under mature trees as an ongoing regimen for treatment can improve mature tree health and growth. In this embodiment, steam is applied with a flow rate of between about 7.5 liters per minute (LPM) and about 30 LPM, preferably steam is applied at a flow rate between about 15 LPM and about 23 LPM. In the most preferred embodiment, steam is applied at a flow rate of about 19 LPM. The steam is heated to a temperature between the ranges of 100° C. and about 150°

C. and is preferably at a temperature of about 125° C. The steam is pressurized to a pressure between about 300 kilopascals (kPa) and about 800 kPa. In the most preferred embodiment, steam pressures are between about 500 kPa and about 600 kPa. Duration of steam application to bryophytes will be in the range of about 30 seconds to about 100 seconds with about 60 seconds being preferred. Immediately following the steam treatment the bryocidal formulation of the present invention will be applied as a slurry onto the soil surface with pressurized spray equipment drawing from a holding tank in the delivery vehicle. The most effective application amount of the bryocidal formulation of the present invention is estimated to be between 5 and 10 kg per hectare depending upon the area and thickness of the moss cover, but exact amounts can be easily determined by the skilled artisan.

Frequency of application of compositions and methods of the present invention can vary, and can easily be determined by one of skill in the art. In a preferred embodiment, frequency of application is expected to be no more than once per year.

In another embodiment, a bryocidal formulation of the present invention includes broadleaf litter or broadleaf mulch. Broadleaf litter can be pretreated with a calcium-rich compound and a carrier of the present invention and spread on the ground. In a preferred embodiment, pretreated broadleaf litter can be compressed into bales designed to break open on impact and applied aerially. Appropriate concentrations of bryocidal formulations and broadleaf litter can be determined easily by one skilled in the art.

In another embodiment, water permeable, opaque biodegradable fabrics, such as weed barriers, can be blended with a calcium-rich compound of a bryocidal formulation of the present invention, and applied to the ground. Appropriate amounts of each ingredient can be determined easily by a skilled artisan.

In another embodiment, the health and/or productivity of trees may be improved by physically scraping bryophytes from the surface of the soil around trees.

The invention is further illustrated by the following non-limited examples. All scientific and technical terms have the meanings as understood by one with ordinary skill in the art. The specific examples which follow illustrate the methods in which the bryocidal compositions of the present invention may be prepared and applied and are not to be construed as limiting the invention in sphere or scope. The methods may be adapted to variation in order to produce compositions embraced by this invention but not specifically disclosed. Further, variations of the methods to produce the same compositions in somewhat different fashion will be evident to one skilled in the art.

EXAMPLES

The examples herein are meant to exemplify the various aspects of carrying out the invention and are not intended to limit the invention in any way.

Example 1

| | Formulation of SILVICURE ™ | | |
|---|---|---|---|
| | Raw Materials | By Weight | Range |
| (1) | Azomite ™ | 2% | 0.5–10% |
| (2) | Polyacrylamide | 3% | 1–10% |
| (3) | Water | 95% | 80–98.5% |

Example 2

Treatment of an Orchard of Mature Trees Using Steam and SILVICURE™

Surface soils in a mature orchard will be treated first with steam using a hand-held steam applicator fed by hoses from a high pressure steamer mounted on a delivery vehicle to be driven slowly through the orchard. Steam will be applied at a flow rate of about 19 liters per minute, at a temperature of about 125° C., at a pressure of about 500 kPa, and a duration of about 60 seconds. Only surface soils that contain moss will be treated. Immediately following steam treatment, all sites will be treated with SILVICURE,™ which will be applied as a slurry onto the soil surface with pressurized spray equipment drawing from a holding tank on a delivery vehicle. SILVICURE™ will be applied at a rate of about 5–10 kg per hectare.

Example 3

Treatment of Roadless Forest Managed for Timber Production

Treatment of forests in roadless areas will be accomplished by applying broadleaf litter pretreated with SILVICURE.™ Bales (5 kg each) of compressed broadleaf litter, containing SILVICURE™, designed to scatter on impact with the soil surface, will be dropped from an aircraft so that the majority of the forest surface is covered by the pretreated broadleaf litter. The amount of litter to be applied will be about 200 to 500 bales per hectare.

The foregoing description is considered as illustrative only of the principles of the invention. The words "comprise," "comprising," "include," "including," and "includes" when used in this specification and in the following claims are intended to specify the presence of one or more stated features, integers, components, or steps, but they do not preclude the presence or addition of one or more other features, integers, components, steps, or groups thereof. Furthermore, since a number of modifications and changes will readily occur to those skilled in the art, it is not desired to limit the invention to the exact construction and process shown described above. Accordingly, all suitable modifications and equivalents may be resorted to falling within the scope of the invention as defined by the claims which follow.

The embodiments of the invention in which an exclusive property or privilege is claimed are defined as follows:

1. A method for remediation of bryophytes, comprising applying a bryocidal formulation, wherein said bryocidal formulation comprises a binding agent and a calcium-rich compound, wherein said calcium-rich compound is incorporated into said bryocidal formulation in sufficient quantity to control said bryophytes.

2. The method of claim 1, wherein said binding agent maintains said calcium-rich compound on the soil surface.

3. The method of claim 1, wherein said calcium-rich compound comprises at least one of the following: micronized hydrated sodium calcium aluminosilicate, crushed hydrated sodium calcium aluminosilicate, micronized limestone, crushed limestone, micronized dolomite, crushed dolomite, micronized lime pulp, crushed lime pulp, micronized seashells, crushed seashells, or a solution of calcium ions.

4. The method of claim 1, wherein said calcium-rich compound is hydrated sodium calcium aluminosilicate.

5. The method of claim 1, wherein said calcium-rich compound has a particle size between about 30 microns and about 5 millimeters.

6. The method of claim 1, wherein said calcium-rich compound is incorporated into said soil treatment in concentrations between about 0.5 percent by weight and about 10.0 percent by weight.

7. The method of claim 1, wherein said binding agent is micronized polyacrylamide.

8. The method of claim 1, wherein said soil treatment further comprises at least one of the following: broadleaf litter, fabric mulch, a wetting agent, and a penetrating agent.

9. The method of claim 1, wherein said binding agent has a particle size between about 30 microns and about 700 microns.

10. The method of claim 1, wherein said binding agent is incorporated into said soil treatment in concentrations between about 1.0 percent by weight and about 10.0 percent by weight.

11. The method of claim 1, wherein said soil treatment further comprises surfactants, wetting agents or other binding agents, penetration agents, translocating agents, adhesives, emulsifiers, suspending agents, thickeners, synergists other moss killers or biocides, such as herbicides, fungicides, bactericides, insecticides and weed killers, hormones, plant growth regulators or plant nutrients.

12. The method of claim 1, wherein said bryophytes to be treated occur under trees or crop plants.

13. The method of claim 12, wherein said soil treatment improves the health of said trees or said crop plants.

14. The method of claim 1, wherein said soil treatment is applied to the soil in an amount between about 5 kilograms and about 10 kilograms per hectare.

15. The method of claim 1, wherein said soil treatment is applied at least once per year.

16. A method for improving the health and productivity of trees and crop plants comprising:

(a) applying a steam treatment to the soil surface around said trees and crop plants; and (b) secondly, applying an bryocidal formulation, wherein said bryocidal formulation comprises a binding agent and a calcium-rich compound, wherein said calcium-rich compound is incorporated into said bryocidal formulation in sufficient quantity to deleteriously impact the growth of bryophytes.

17. The method of claim 16, wherein said steam treatment comprises:

(a) heating water to greater than 100° C., (b) pressurizing the steam to between about 300 kPa and about 800 kPa;

(c) flowing the steam between about 7.5 LPM and about 30 LPM; and (d) applying the steam to the ground for a duration between about 30 seconds and about 100 seconds.

18. A method of improving the health and productivity of saplings and mature trees comprising:

applying steam to bryophytes found growing on the soil surrounding saplings and mature trees; and applying a bryocidal formulation comprising:

a polyacrylamide in a concentration of about 3.0 percent by weight;

hydrated sodium calcium aluminosilicate in a concentration of about 2.0 percent by weight; and a solvent in a concentration of about 95.0 percent by weight following the application of steam.

* * * * *